United States Patent [19]

Dingwall et al.

[11] 4,265,769
[45] May 5, 1981

[54] METHOD OF TREATING AQUEOUS SYSTEMS WITH PHOSPHONOADIPIC ACIDS

[75] Inventors: John G. Dingwall, Sale; Barry Cook, Manchester; Alan Marshall, Macclesfield, all of England

[73] Assignee: Ciba-Geigy Corporation, Ardsley, N.Y.

[21] Appl. No.: 87,133

[22] Filed: Oct. 22, 1979

Related U.S. Application Data

[60] Division of Ser. No. 15,016, Feb. 26, 1979, Pat. No. 4,208,344, which is a continuation of Ser. No. 862,795, Dec. 21, 1977, abandoned.

[30] Foreign Application Priority Data

Dec. 24, 1976 [GB] United Kingdom ............... 54106/76

[51] Int. Cl.$^3$ ............................................. B01D 21/01
[52] U.S. Cl. .................................... 210/699; 252/175; 252/180; 252/389 A; 260/507.4 R; 422/15; 560/190
[58] Field of Search ....................... 252/180, 175, 389; 260/502.4 R; 560/190; 422/12; 210/58, 699

[56] References Cited

U.S. PATENT DOCUMENTS

| | | | |
|---|---|---|---|
| 2,616,918 | 11/1952 | Johnston | 252/389 |
| 3,714,066 | 1/1973 | King | 252/389 A |
| 4,052,160 | 10/1977 | Cook et al. | 422/15 |

FOREIGN PATENT DOCUMENTS

| | | |
|---|---|---|
| 1039692 | 9/1958 | Fed. Rep. of Germany. |
| 1038692 | of 1960 | Fed. Rep. of Germany. |
| 2217692 | 4/1972 | Fed. Rep. of Germany. |
| 2225645 | 1/1974 | Fed. Rep. of Germany. |
| 2310450 | 8/1974 | Fed. Rep. of Germany. |
| 2505435 | 8/1976 | Fed. Rep. of Germany. |
| 1423495 | 2/1976 | United Kingdom. |
| 1522066 | 8/1978 | United Kingdom. |

OTHER PUBLICATIONS

Opitz et al. Ann 640, 36 (1961).
Kabachnik et al. CA 47, 4848e (1953).

Primary Examiner—Mayer Weinblatt
Attorney, Agent, or Firm—Luther A. R. Hall

[57] ABSTRACT

A compound or mixture of compounds of the general formula:

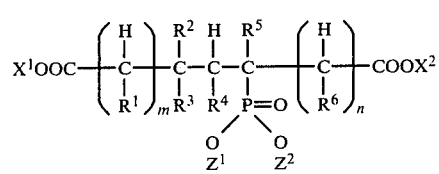

in which m and n may be 0 or 1 but both cannot be 1, $R^1$, $R^2$, $R^3$, $R^4$, $R^5$ and $R^6$ are independently H or $CH_3$, $X^1$, $X^2$, $Z^1$ and $Z^2$ are independently hydrogen or straight or branched chain $C_1$–$C_4$ alkyl; and the water-soluble inorganic or organic salts thereof, with the proviso that at least one of $R^1$, $R^2$, $R^3$, $R^4$, $R^5$ must be $CH_3$, and when m and n are both 0, $R^2$ and $R^3$ are each methyl and $R^4$ and $R^5$ have their previous significance, when added to an aqueous system imparts one or more of the following beneficial effects to be treated system:

(a) the corrosion of ferrous metals in contact with the system is inhibited;
(b) the precipitation of scale-forming salts of calcium, magnesium, barium and strontium from the treated aqueous system is inhibited; and,
(c) inorganic materials present in the treated aqueous system are dispersed.

14 Claims, No Drawings

METHOD OF TREATING AQUEOUS SYSTEMS WITH PHOSPHONOADIPIC ACIDS

This is a divisional of application Ser. No. 015,016, filed on Feb. 26, 1979, now U.S. Pat. No. 4,208,344, issued June 17, 1980, which in turn is a continuation of application Ser. No. 862,795, filed on Dec. 21, 1977, now abandoned.

The present invention relates to new phosphonic/carboxylic acids having value as additives to aqueous systems and processes for their preparation.

According to the present invention there is provided a compound or mixture of compounds of the general formula:

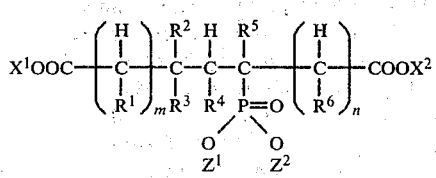

in which m and n may be 0 or 1 but both cannot be 1, $R^1$, $R^2$, $R^3$, $R^4$, $R_5$ and $R^6$ are independently H or $CH_3$, $X^1$, $X^2$, $Z^1$ and $Z^2$ are independently hydrogen or straight or branched chain $C_1$–$C_4$ alkyl; and the water-soluble inorganic or organic salts thereof, with the proviso that at least one of $R^1$, $R^2$, $R^3$, $R^4$, $R^5$ must be $CH_3$, and when m and n are both 0, $R^2$ and $R^3$ are each methyl and $R^4$ and $R^5$ have their previous significance.

When $X^1$, $X^2Z^1$ or $Z^2$ is $C_1$–$C_4$ alkyl this may be for example methyl, ethyl, propyl, isopropyl, butyl, sec-butyl or tertiary butyl.

Examples of compounds of formula I when m=1 and n=0 are as follows:
2-methyl-2-phosphonoadipic acid
3-methyl-2-phosphonoadipic acid
4-methyl-2-phosphonoadipic acid
5-methyl-2-phosphonoadipic acid
2,4-dimethyl-2-phosphonoadipic acid
2,3-dimethyl-2-phosphonoadipic acid
4,4-dimethyl-2-phosphonoadipic acid
2,4,4-trimethyl-2-phosphonoadipic acid
2,4,4,5-tetramethyl-2-phosphonoadipic acid
dimethyl 2-methyl-2-dimethylphosphonoadipate
2,4-dimethyl-2-monoethylphosphonoadipic acid
diethyl 2-diethylphosphono-2-methyl-adipate ethyl 5-carbomethoxy-2-diethylphosphono-4-methylpentanoate
ethyl 5-carbomethoxy-2-diethylphosphono 2,4-dimethylpentanoate
diethyl 2-diethylphosphono-4,4-dimethyladipate
diethyl 2-diethylphosphono-2,4,4-trimethyladipate Examples of compounds of formula I when m=0 and n=1 are as follows:
3-phosphonoadipic acid
2-methyl-3-phosphonoadipic acid
3-methyl-3-phosphonoadipic acid
4-methyl-3-phosphonoadipic acid
5-methyl-3-phosphonoadipic acid
3,5-dimethyl-3-phosphonoadipic acid
3,4-dimethyl-3-phosphonoadipic acid
2,5-dimethyl-3-phosphonoadipic acid
3,5,5-trimethyl-3-phosphonoadipic acid
2,3,5,5-tetramethyl-3-phosphonoadipic acid
3,5,5-trimethyl-3-dimethylphosphonoadipic acid
diethyl 3-diethylphosphonoadipate
3,5,5-trimethyl-3-monomethylphosphonoadipic acid An example of a compound when m and n=0 is 2,4,4-trimethyl-2-phosphonoglutaric acid.

Preferred compounds of formula I are those in which $X^1$, $X^2$, $Z^1$ and $Z^2$ are hydrogen. More preferred compounds are those in which $X^1$, $X^2$, $Z^1$ and $Z^2$ are hydrogen and $R^1$, $R^4$ and $R^6$ are hydrogen. Especially preferred compounds are those in which $X^1$, $X^2$, $Z^1$, $Z^2$, $R^1$, $R^4$ and $R^6$ are hydrogen and $R^2$, $R^3$ and $R^5$ are methyl, namely 2,4,4-trimethyl-2-phosphonoadipic acid, 3,5,5-trimethyl-3-phosphonoadipic acid and 2,4,4-trimethyl-2-phosphonoglutaric acid or mixtures thereof in any proportion.

Other valuable mixtures of compounds of formula I are a mixture of 2-methyl-2-phosphonoadipic acid and 3-methyl-3-phosphonoadipic acid, and a mixture of 2,4-dimethyl-2-phosphonoadipic acid and 3,5-dimethyl-3-phosphonoadipic acid.

A further valuable mixture consists of 3-phosphonoadipic acid of the present invention together with 2-phosphonoadipic acid.

The water-soluble inorganic salts of the compounds of formula I may be the alkali metal salts, for example the sodium and potassium salts and the ammonium salts.

The water-soluble organic salts of the compounds of formula I may be the salts of amines, for example, mono-, di- or triethanolamines.

The present invention further provides a process for the preparation of a compound of formula I where m is 1 or 0, n is 0, $R^1$, $R^2$, $R^3$, $R^4$ and $R^5$ have their previous significance and $X^1$, $X^2$, $Z^1$ and $Z^2$ are $C_1$–$C_4$ alkyl, which comprises reacting a compound having the formula:

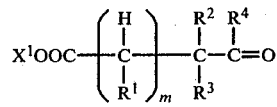

wherein $X^1$ is $C_1$–$C_4$ alkyl, m is 1 or 0 and $R^1$, $R^2$, $R^3$ and $R^4$ have their previous significance, with a trialkylphosphonoacetate having the formula:

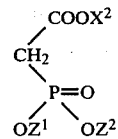

wherein $X^2$, $Z_1$ and $Z^2$ are $C_1$–$C_4$ alkyl in the presence of a condensation catalyst, conveniently a mixture of titanium tetrachloride and a tertiary amine such as N-methylmorpholine, to give an olfein having the formula:

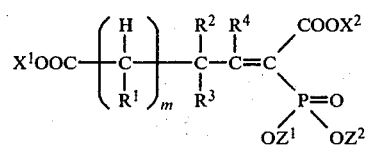

followed by catalytic hydrogenation to give a compound having the formula:

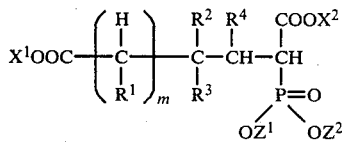

and optionally methylating compound (V) in the presence of a base to give a compound having the formula:

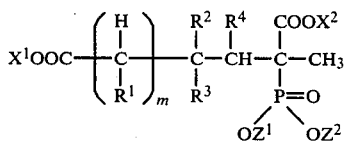

where, in the compounds of formulae IV, V and VI, $X^1$, $X^2$, $Z^1$ and $Z^2$ are $C_1$–$C_4$ alkyl and $R^1$, $R^2$, $R^3$, $R^4$ and m have their previous significance.

The methylating agent may be, for example, dimethyl sulphate or a methyl halide such as methyl iodide and the base is conveniently sodium hydride.

Subsequent hydrolysis of Compound V or Comound VI with aqueous acid or base gives the compounds of formula I in which m is 1 or 0, n is 0, $R^1$, $R^2$, $R^3$, $R^4$ and $R^5$ have their previous significance and at least one of $X^1$, $X^2$, $Z^1$ or $Z^2$ is hydrogen. The water soluble inorganic or organic salts may be obtained by neutralisation or partial neutralisation of these acids.

The present invention further provides a process for the preparation of a compound of formula I where m is 1, n is 0, $R^2$ is hydrogen, $R^1$, $R^3$, $R^4$ and $R^5$ have their previous significance, and $X^1$, $X^2$, $Z^1$ and $Z^2$ are $C_1$–$C_4$ alkyl, which comprises reacting a substituted alkyl halide having the formula:

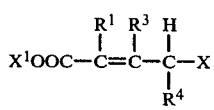

wherein X is bromo- or chloro-, $X^1$ is $C_1$–$C_4$ alkyl and $R^1$, $R^3$ an $R^4$ have their previous significance, and the anion formed by treating a compound having the formula

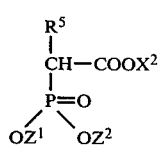

wherein $X^2$, $Z^1$ and $Z^2$ are $C_1$–$C_4$ alkyl and $R^5$ has its previous significance with a strong base such as sodium ethoxide to give a compound having the formula:

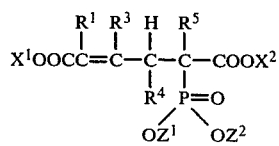

followed by catalytic hydrogenation to give a compound having the formula:

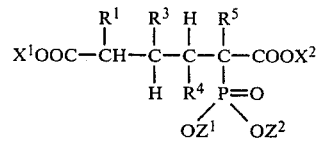

where, in the compounds of formulae IX and X, $X^1$, $X^2$, $Z^1$ and $Z^2$ are $C_1$–$C_4$ alkyl and $R^1$, $R^3$, $R^4$ and $R^5$ have their previous significance.

Subsequent hydrolysis of the compound of formula X with aqueous acid or base gives the compounds of formula I in which m is 1, n is 0, $R^2$ is hydrogen, $R^1$, $R^3$, $R^4$ and $R^5$ have their previous significance and at least one of $X^1$, $X^2$, $Z^1$ or $Z^2$ is hydrogen. The water soluble inorganic or organic salts may be obtained by neutralisation or partial neutralisation of these acids.

The present invention further provides a process for the preparation of a compound of formula I when m is 0, n is 1, $R^2$, $R^3$, $R^4$, $R^5$, $R^6$, $X^1$ and $X^2$ have their previous significance and $Z^1$ and $Z^2$ are $C_1$–$C_4$ alkyl which comprises reacting an olefin having the formula:

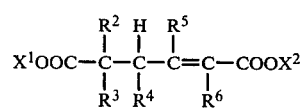

wherein $X^1$ and $X^2$ are hydrogen or $C_1$–$C_4$ alkyl and $R^2$, $R^3$, $R^4$, $R^5$ and $R^6$ have their previous significance, with a compound having the formula:

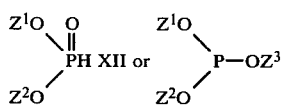

wherein $Z^1$, $Z^2$ and $Z^3$ are $C_1$–$C_4$ alkyl to give a compound having the formula:

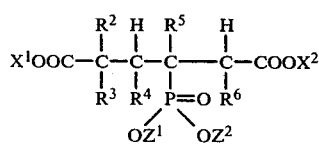

wherein $R^2$, $R^3$, $R^4$, $R^5$, $R^6$, $X^1$ and $X^2$ have their previous significance and $Z^1$ and $Z^2$ are $C_1$–$C_4$ alkyl.

Compounds of formula XI can be made by conventional methods.

Subsequent hydrolysis of compound XIV with aqueous acid or base gives the compounds of formula I in which m is 0, n is 1, $R^2$, $R^3$, $R^4$, $R^5$ and $R^6$ have their previous significance and at least one of $X^1$, $X^2$, $Z^1$ or $Z^2$ is hydrogen. The water soluble inorganic or organic salts may be obtained by neutralisation or partial neutralisation of these acids.

The present invention further provides a process for the preparation of the compounds of formula I wherein m, n, $R^1$, $R^2$, $R^3$, $R^4$, $R^5$, $R^6$, $Z^1$ and $Z^2$ have their previous significance and $X^1$ and $X^2$ are hydrogen, by oxidation of a substituted cyclohexanone having the formula:

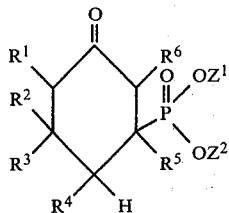

wherein $R^1$, $R^2$, $R^3$, $R^4$, $R^5$, $R^6$, $Z^1$ and $Z^2$ have their previous significance.

The compounds of formula XV are prepared by methods well known in the organophosphorus literature, e.g. by base catalysed addition of a dialkyl phosphite to the appropriate cyclohex-2-enone.

Suitable oxidising agents are, for example, concentrated nitric acid, chromic acid/sulphuric acid mixtures, sodium hypochlorite, sodium hypobromite, hydrogen peroxide, peracetic acid and oxygen in the presence of a transition metal catalyst for example cobalt or manganese acetates.

When nitric acid is used as the oxidising agent mixtures of compounds of formula I are usually formed in varying proportions and the individual components may, if desired, be isolated by conventional processes such as fractional crystallisation.

By suitable selection of the conditions under which the oxidation takes place, the proportions of the individual components may be varied.

In this process, when $R^1$, $R^2$, $R^3$, $R^4$, $R^5$, $R^6$, $Z^1$ and $Z^2$ are all hydrogen, 3-phosphonoadipic acid of this invention is formed together with 2-phosphonoadipic acid.

The oxidation with nitric acid may conveniently be carried out using from 20% to 70%, preferably from 40% to 70% aqueous nitric acid at a temperature from 0° to 120° C., preferably from 50° C. to 70° C., advantageously in the presence of an oxidation catalyst such as a vanadium, manganese or copper compound.

When oxidising a compound of formula XV wherein $Z^1$ and $Z^2$ are $C_1$–$C_4$ alkyl with nitric acid, a suitable solvent may be added to aid solubilisation, for example, acetic acid.

The acids formed in this process may be converted to the esters of formula I in which $X^1$, $X^2$, $Z^1$ and $Z^2$ are $C_1$–$C_4$ alkyl by treatment with an esterifying agent e.g. a trialkyl orthoformate.

The compounds of formula I or salts thereof have been found to impart beneficial properties to aqueous systems to which they are added.

The present invention therefore provides a method of treating an aqueous system which comprises adding to the aqueous system a minor proportion of a compound or mixture of compounds of formula I or their water soluble salts. The amount of compound or mixture of compounds of formuula I is conveniently from 0.1 to 1000 parts, preferably 1 to 1000 parts and most preferably 1 to 50 parts by weight per million parts by weight of aqueous system.

The addition of a compound of formula I, or a water-soluble salt thereof, to an aqueous system, has been found to impart one or more of the following beneficial effects to the treated system: (a) the corrosion of ferrous metals in contact with the system is inhibited; (b) the precipitation of scale-forming salts of calcium, magnesium, barium and strontium from the treated aqueous system is inhibited; and (c) inorganic materials present in the treated aqueous system are dispersed.

The compounds of formula I may be used alone or in conjunction with other compounds known to be useful in water treatment. Corrosion inhibitors may be used such as, for example, water soluble zinc salts; phosphates; polyphosphates; phosphonic acids and their salts for example acetodiphosphonic acid, nitrilotris methylene phosphonic acid and methylamino dimethylene phosphonic acid; phosphonocarboxylic acids and their salts, for example, those described in DT-OS No. 2632774.2, and 3-phosphonobutane 1,2,4-tricarboxylic acid; chromates, for example, sodium chromate; nitrites, for example, sodium nitrite; nitrates, for example sodium nitrate, benzotriazole, bis-benzotriazole or copper-deactivating benzotriazole derivatives; N-acyl sarcosines; triethanolamines; fatty amines; and polycarboxylic acids, for example, polymaleic acid and polyacrylic acid as well as their respective alkali metal salts.

Dispersing and/or threshold agents may be used, such as for example polymerised acrylic acid and its salts, hydrolysed polyacrylonitrile, polymerised methacrylic acid and its salts, polyacrylamide and co-polymers thereof from acrylic and methacrylic acids, lignin sulphonic acid and its salts, tannin, naphthalene sulphonic acid/formaldehyde condensation products, starch and its derivatives, and cellulose. Specific threshold agents such as for example, hydrolysed polymaleic anhydride and its salts, alkyl phosphonic acids, 1-aminoalkyl, 1,1-diphosphonic acid and their salts and alkali metal polyphosphates, may also be used.

Compounds of formula I may also be used with precipitating agents such as alkali metal orthophosphates, carbonates and hydroxides; oxygen scavengers such as alkali metal sulphites and hydrazine; sequestering agents such as nitrilotriacetic acid and their salts and ethylene diamine tetraacetic acid and its salts; antifoaming agents such as distearylsebacamide, distearyl adipamide and related products derived from ethylene oxide condensations; silicones; and fatty alcohols, such as capryl alcohols and their ethylene oxide condensates.

Biocides may be used such as chlorine, ozone, acrolein, organo sulphur compounds for example methylene bis thiocyanate; dithiocarbamates; chlorinated phenols and bisphenols, for example, b 2,2'-dihydroxy-5,5'-dichloro-diphenyl methane and pentachlorophenol; organometallic compounds for example tri-butyl tin oxide; and quaternary ammonium compounds.

When the compound of formula I used is 3-phosphonoadipic acid, it may conveniently be used in admixture with 2-phosphonoadipic acid, which mixture is formed by the oxidation of the substituted cyclohexanone of formula XV, wherein $R^1$, $R^2$, $R^3$, $R^4$, $R^5$, $R^6$, $Z^1$ and $Z^2$ are each hydrogen.

The compounds of formula I could find use in e.g. cooling water systems; steam generating plant; sea-water evaporators; and hydrostatic cookers.

The following Examples further illustrate the present invention. Parts and percentages, shown therein are by weight unless otherwise stated.

EXAMPLE 1

Diethyl 1,3,3-trimethyl-5-oxocyclohexanephosphonate (B.Pt. 128°–30°/0.6 mm) was prepared by base catalysed addition of diethyl phosphite to isophorone. Hydrolysis of this ester with c.HCl gave 1,3,3-trimethyl-5-oxocyclohexanephosphonic acid (M.Pt. 167°–8° C.).

22 parts of 1,3,3-trimethyl-5-oxocyclohexanephosphonic acid were added portion wise, over 6 hours, to a stirred solution of 0.05 parts of ammonium metavanadate in 32 parts of 70% nitric acid at 55°–60° C.; when the addition was complete the resulting solution was heated at 55°–60° C. for a further 5 hours, cooled to room temperature, and diluted by the addition of 50 parts of water. This solution was evaporated to dryness, the solid residue redissolved in 100 parts of water and again evaporated to dryness to give 21.7 parts of a hygroscopic solid which was substantially a 1:1 mixture of 2,4,4-trimethyl-2-phosphonoadipic acid and 3,5,5-trimethyl-3-phosphonoadipic acid which had $^{31}$P chemical shifts of $-25$ and $-32$ ppm respectively and a minor proportion of 2,4,4-trimethyl-2-phosphono glutaric acid having a $^{31}$P chemical shift of $-24$ ppm.

EXAMPLE 2

Diethyl 1-methyl-5-oxocyclohexanephosphonate (B.Pt. 130°–2°/0.8 mm) was prepared by the base catalysed addition of diethylphosphite to 3-methyl-2-cyclohexen-1-one. Hydrolysis of this ester with concentrated HCl gave 1-methyl-5-oxocyclohexanephosphonic acid as a viscous oil.

Oxidation of 19.2 parts of the phosphonic acid with 70% nitric acid, as in Example 1, gave 20.7 parts of an hygroscopic solid which was substantially a 1:1 mixture of 2-methyl-2-phosphonoadipic acid and 3-methyl-3-phosphonoadipic acid which had $^{31}$P chemical shifts of $-24$ ppm and $-32$ ppm respectively.

EXAMPLE 3

Diethyl 1,3-dimethyl-5-oxocyclohexanephosphonate (B. pt. 120°/0.1 mm) was prepared by the base catalysed addition of diethylphosphite to 3,5-dimethyl-2-cyclohexen-1-one. Hydrolysis of the ester in concentrated HCl gave 1,3-dimethyl-5-oxocyclohexanephosphonic acid as a viscous oil.

Oxidation of 18.7 parts of the phosphonic acid with 70% nitric acid, as in Example 1, gave 17.6 parts of an hygroscopic solid which was substantially a 1:1 mixture of 2,4-dimethyl-2-phosphonoadipic acid and 3,5-dimethyl-3-phosphonoadipic acid, having $^{31}$P chemical shifts of $-25$ ppm and $-31$ ppm respectively.

EXAMPLE 4

A concentrated aqueous solution of the mixed product from Example 1 was allowed to stand at room temperature for several days during which time a white solid precipitated. This was collected by filtration and dried to give 3,5,5-trimethyl-3-phosphonoadipic acid (m.pt. 167°–8° C., decomposing, $^{31}$P chemical shift of $-32$ ppm) which had the following elemental analysis by weight.

|  | C | H | P |
| --- | --- | --- | --- |
| Required for $C_9H_{17}O_7P \cdot 1\frac{1}{2}H_2O$ | 36.61 | 6.78 | 10.50% |
| Found | 36.71 | 6.66 | 10.43% |

EXAMPLE 5

Diethyl 5-oxocyclohexanephosphonate (B.Pt. 142°–3° C./0.2 mm) was prepared by the base catalysed addition of diethylphosphite to 2-cyclohexen-1-one.

Oxidation of 23.3 parts of the phosphonic ester with 70% nitric acid as in Example 1, followed by hydrolysis with concentrated hydrochloric acid gave 22.6 parts of a viscous oil which was substantially a 1:1 mixture of 2-phosphonoadipic acid and 3-phosphonoadipic acid, having $^{31}$P chemical shifts of $-20$ ppm and $-30$ ppm respectively.

EXAMPLE 6

Ethyl 4-bromocrotonate (19.3 parts) was added dropwise at 25°–30° C. to a solution of the sodium salt of ethyl 2-diethylphosphonopropionate, prepared from 23.8 parts of ethyl 2-diethylphosphonopropionate and 5.3 parts of sodium hydride (50% in oil) in dioxan. The resulting solution was heated at reflux for 18 hr., after which time the sodium bromide was removed by filtration and the solution concentrated in vacuo. The residual oil was distilled to give 12.7 parts of ethyl 5-carboethoxy-2-diethylphosphono-2-methylpent-4-enoate boiling at 158°/0.2 mm. Hydrogenation of 12 parts of this material over 5% palladium on carbon gave 7.2 parts of diethyl 2-diethylphosphono-2-methyladipate boiling at 146°–52° C./0.05 mm; subsequent hydrolysis of 5 parts of this in concentrated hydrochloric acid gave 3.7 parts of 2-methyl-2-phosphonoadipic acid as a glassy solid which had a $^{31}$P chemical shift of $-24$ ppm.

EXAMPLE 7

Ethyl 5-carbomethoxy-2-diethylphosphono-4-methylpent-4-enoate (boiling at 160° C./0.3 mm) was prepared by reaction of methyl 4-bromo-3-methylcrotonate with the anion of triethylphosphonoacetate in dioxan as in Example 6.

Hydrogenation over 10% palladium on carbon gave ethyl 5-carbomethoxy-2-diethylphosphono-4-methylpentanoate, boiling at 166° C./0.2 mm (Found: P, 8,96%; $C_{14}H_{26}O_7P$ required: P, 9.18%).

Hydrolysis of 10 parts of this material with concentrated hydrochloric acid gave 8.3 parts of 4-methyl-2-phosphonoadipic acid as a glassy solid having a $^{31}$P chemical shift of $-20$ ppm and the following elemental analysis by weight.

Found: C, 34.94%; H, 5.99%: $C_7H_{13}O_7P$ requires: C, 35.01%; H, 5.46%.

EXAMPLE 8

Ethyl 5-carbomethoxy-2-diethylphosphono-2,4-dimethylpent-4-enoate (boiling at 160°–4° C./0.2 mm) was prepared by the reaction of methyl 4-bromo-3-methylcrotonate with the anion of ethyl 2-diethylphosphonopropionate in dioxan as in Example 6. Hydrogenation over platinum dioxide gave ethyl 5-carbomethoxy-2-diethylphosphono-2,4- dimethylpentanoate, boiling at 146° C./0.1 mm. Subsequent hydrolysis with concentrated hydrochloric acid gave 2,4-dimethyl-2-phosphonoadipic acid as a glassy solid, having a $^{31}$P chemical shift of $-25$ ppm and the following elemental analysis by weight:

Found: C, 35.01%; H, 5.82%; P, 11.00%. $C_8H_{15}O_7P \cdot H_2O$ requires: C, 35.29%; H, 6.25%; P, 11.39%.

EXAMPLE 9

A solution of titanium tetrachloride (7.7 parts by vol.) in dry carbon tetrachloride (18 parts by vol.) was added dropwise at 0° C. to dry tetrahydrofuran (140 parts by vol.). To this solution at 0° C. was added dropwise a mixture of triethylphosphonoacetate (7.9 parts) and ethyl 3-formyl-3-methylbutyrate (5.6 parts) (prepared by the method of G. Opitz et al., Ann. 1961, 649, 36) followed by addition of a solution of N-methylmorpholine (15.4 parts by vol.) in dry tetrahydrofuran (26 parts by vol.) over 30 min. The resulting mixture was stirred at 0° C. for 22 hr., water (50 parts by vol.) was added, and stirred at 20°–25° C. for 30 min. This was then ether extracted (4×50 parts by vol.) and the bulked ether extracts washed with water (2×25 parts by vol.) and dried over magnesium sulphate. The ether was removed by evaporation and the residual oil distilled to give 7.2 parts of ethyl 5-carboethoxy-2-diethylphosphono-4,4-dimethyl-pent-2-enoate, boiling at 142°–4° C./0.1 mm, as a cis-trans mixture.

Hydrogenation of this (10.2 parts) over platinum dioxide catalyst gave diethyl 2-diethylphosphono-4,4-dimethyladipate boiling at 144°–6° C./0.1 mm having a $^{31}P$ chemical shift of $-23$ ppm. Hydrolysis of this ester in concentrated hydrochloric acid gave 4,4-dimethyl-2-phosphonoadipic acid as a glassy solid having a $^{31}P$ chemical shift of $-21$ ppm.

EXAMPLE 10

Diethyl 2-diethylphosphono-4,4-dimethyladipate (3.6 parts) (See Example 9) was added dropwise to a suspension of sodium hydride (0.6 parts, 50% in oil) in dry dioxan (100 parts by volume) contaning methyliodide (14.2 parts) over 2 hr. at room temperature. The resulting solution was stirred at room temperature for 18 hr. then heated to reflux for 2 hr., cooled, the solids removed by filtration and the filtrate concentrated in vacuo. Distillation of the residual oil gave 3 parts of diethyl 2-diethylphosphono-2,4,4-trimethyladipate, boiling at 137°–8° C./0.03 mm having a $^{31}P$ chemical shift of $-26$ ppm and having the following elemental analysis by weight.

Found: C, 53.57; H, 8.91; P, 7.85%. $C_{17}H_{33}O_7P$ requires: C, 53,67; H, 8.74; P, 8.14%.

Hydrolysis of this ester in concentrated hydrobromic acid gave 2,4,4-trimethyl-2-phosphonoadipic acid as a hygroscopic solid having a $^{31}P$ chemical shift of $-25$ ppm.

EXAMPLE 11

Demonstration of Corrosion Inhibitor Activity of Product of Example 1

Corrosion inhibitor activity of the product of Example 1 was demonstrated in the following way by the Aerated Solution Bottle Test and using a standard corrosive water made up as follows:
20 g $CaSO_4 2H_2O$
15 g $MgSO_4 7H_2O$
4.6 g $NaHCO_3$
7.7 g $CaCl_2 6H_2O$
45 gallons distilled water Mild steel coupons, 5 cms×2.5 cms are scrubbed with pumice immersed for one minute in hydrochloric acid and then rinsed, dried and weighed.

The desired proportion of additive combination is dissolved in 100 ml of standard corrosive water. A steel coupon is suspended in the solution, and the whole is stored in a bottle in a thermostat at 40° C. During the storage period, air is passed into the solution at 500 ml/minute, the passage of the air being screened from the steel coupon; any water losses by evaporation are replaced as they occur with distilled water from a constant head apparatus.

After 48 hours, the steel coupon is removed, scrubbed with pumice, immersed for one minute in hydrochloric acid inhibited with 1% by weight of hexamine and then rinsed, dried and reweighed. A certain loss in weight will have occurred. A blank test i.e. immersion of a mild steel specimen in the test water in the absence of any potential corrosion inhibitor, is carried out with each series of tests. The corrosion rates are calculated in milligrams of weight loss/sq. decimeter/day (m.d.d) but for convenience the results are shown as percentage protection, which is defined as follows:

$$\% \text{ Protection} = \frac{\text{Corrosion rate for blank (in mdd)} - \text{corrosion rate for sample (in mdd)}}{\text{Corrosion rate for blank (in mdd)}} \times 100$$

The results obtained using 100 parts per million of the product of Examples 1, 2 and 4 are given in Table I.

TABLE I

| Product (100 ppm) | % Protection |
| --- | --- |
| Product of Example 1 | 92 |
| Product of Example 2 | 93 |
| Product of Example 4 | 86 |

EXAMPLE 12

Demonstration of dispersant activity for iron oxide

To carry out this test a sample of iron oxide is prepared as follows:

An excess of 0.88 ammonium hydroxide solution is added to 500 milliliters of a 20% weight/volume solution of $FeSO_4.7H_2O$ with vigorous stirring. The solution is brought to the boil and filtered under reduced pressure through a Whatman No. 54 filter paper. The filtered precipitate is washed with hot water several times and then sucked dry. The filter cake is dried in an oven at 105° C. for 2 to 3 hours on a watch glass, then ground in a mortar and pestle to a fine powdery consistency. 0.20 grams of this iron oxide are weighed out into a 100 milliliter measuring cylinder, distilled water added up to the 80 milliliter level and the cylinder placed in a water bath at 50° C. When the solution has equilibrated at 50° C., 20 milliliters of a solution containing the additive is added and the suspension stirred thoroughly with a glass rod. The cylinder is allowed to stand a further 2 minutes, then removed from the water bath and the contents allowed to settle. After 20 minutes the optical density of the suspension is measured at 500 nm in a 1 centimeter cell. In the absence of additive the optical density was 0.35 and in the presence of the product of Example 1, at weight ratio of 1 part product of Example 1:20 part iron oxide, the optical density was 0.78. This demonstrates the ability of the product of Example 1 to keep iron oxide in suspension.

EXAMPLES 13 AND 14

Evaluation of scale inhibiting activity

The compounds were evaluated as scale inhibitors in a recirculating water evaporative cooling test ring simulating the major features of an industrial cooling system.

The rig comprises an electrically heated heat exchanger, cooling tower, tower sump, reservoir, and make up and blowdown facilities. Feed water to the rig had the following analysis:

| pH | PA | TA | TH | $Cl^-$ |
| --- | --- | --- | --- | --- |
| 7.39 | nil | 125 | 157 | 37 |

In the analytical data, the signification of the abbreviations used is as follows:

| PA is phenol alkalinity | (ppm of CaCO₃) |
|---|---|
| TA is total alkalinity | (ppm of CACO₃) |
| TH is total hardness | (ppm of CACO₃) |

The operating parameters for the results described were:

| Recirculation rate: | 106 gallons per hour |
|---|---|
| Water Velocity: | 1.4 feet per second |
| Maximum water temperature: | 46° C. |
| Temperature rise through heater | 3° C. |
| Evaporation Rate: | 1.8 liters per hour |
| Concentration factor: | 3.0 |

The quantity of compound under test necessary to give the required dose level is added to 200 liters of feed water in the make up tank. The rig is then filled (20 liters capacity) and run until the required concentration factor has been reached. Constant volume is maintained in the system by means of an automatic level control. The heat exchanger is then stripped down and the weight of scale deposited determined. After cleaning and reassembling the heat exchanger, the rig is restarted with the blowdown pump switched on and set to maintain the system at a concentration factor of 3. The rig is then operated until 100 liters of feed water have been used. The weight of scale deposited on the heat exchanger is then determined. Two weights of scale are thus obtained for each test, one whilst the rig is being concentrated and the second after a period of operation at the desired concentration factor. The results are expressed as a scaling rate, that is, milligrams of scale deposited per liter of feed water added.

The scale deposited in these tests consists mainly of calcium carbonate and the results are given in Table II.

| Example | Additive | Dose to feed ppm solids | Scaling rate milligrams/liter Concentration | Run |
|---|---|---|---|---|
| | Nil | Nil | 32.8 | 35.1 |
| 13 | Product of Example 1 | 5 | 1.5 | 5.7 |
| | | 2.5 | 8.4 | 7.5 |
| 14 | Product of Example 4 | 10 | 2.4 | 2.4 |
| | | 5 | 1.8 | 3.4 |
| | | 2.5 | 8.9 | 2.3 |

What is claimed is:

1. A method of treating an aqueous system in order to provide the inhibition of corrosion of ferrous metals in contact therewith; the inhibition of precipitation of calcium, magnesium, barium or strontium salts from said aqueous system; and the dispersion of inorganic materials present in said aqueous system which comprises adding to an aqueous system (a), per million parts by weight of said aqueous system, from 0.1 to 1000 parts of (b) a compound or mixture of compounds of the formula

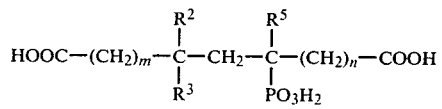

in which m and n may be 0 or 1, but both cannot be 1, and $R^2$, $R^3$ and $R^5$ are independently hydrogen or methyl; or the water-soluble inorganic or organic salts thereof; with the proviso that at least one of $R^2$, $R^3$ and $R^5$ must be methyl, and when m and n are both 0, all of $R^2$, $R^3$ and $R^5$ are methyl.

2. A method according to claim 1 wherein component (b) is a compound or mixture of compounds selected from the group consisting of 2,4,4-trimethyl-2-phosphonoadipic acid, 3,5,5-trimethyl-3-phosphonoadipic acid and 2,4,4-trimethyl-2-phosphonoglutaric acid.

3. A method according to claim 1 wherein component (b) is a compound or mixture of compounds selected from the group consisting of 2-methyl-2-phosphonoadipic acid and 3-methyl-3-phosphonoadipic acid.

4. A method according to claim 1 wherein component (b) is a compound or mixture of compounds selected from the group consisting of 2,4-dimethyl-2-phosphonoadipic acid and 3,5-dimethyl-3-phosphonoadipic acid.

5. A method according to claim 1 wherein component (b) is a compound or mixture of compounds in which $R^2$, $R^3$ and $R^5$ are methyl.

6. A method according to claim 1 wherein component (b) is a compound or mixture of compounds wherein the water-soluble inorganic salts are the sodium, potassium or ammonium salts.

7. A method according to claim 1 wherein component (b) is a compound or mixture of compounds wherein the water-soluble organic salts are the salts of mono-, di- or triethanolamine.

8. A composition comprising an aqueous system, inhibiting the corrosion of ferrous metals in contact therewith; inhibiting the precipitation of calcium, magnesium, barium or strontium salts from said aqueous system; and dispersing inorganic materials present in said aqueous system, which comprises (a) a major proportion of water; and
(b) from 0.1 to 1000 parts, per million parts by weight of water, of a compound or mixture of compounds of the formula

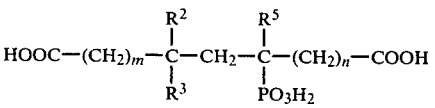

in which m and n may be 0 or 1, but both cannot be 1, and $R^2$, $R^3$ and $R^5$ are independently hydrogen or methyl; or the water-soluble inorganic or organic salts thereof; with the proviso that at least one of $R^2$, $R^3$ and $R^5$ must be methyl, and when m and n are both 0, all of $R^2$, $R^3$ and $R^5$ are methyl.

9. A composition according to claim 8 wherein component (b) is a compound or mixture of compounds selected from the group consisting of 2,4,4-trimethyl-2-phosphonoadipic acid, 3,5,5-trimethyl-3-phosphonoadipic acid and 2,4,4-trimethyl-2-phosphonoglutaric acid.

10. A composition according to claim 8 wherein component (b) is a compound or mixture of compounds selected from the group consisting of 2-methyl-2-phosphonoadipic acid and 3-methyl-3-phosphonoadipic acid.

11. A composition according to claim 8 wherein component (b) is a compound or mixture of compounds selected from the group consisting of 2,4-dimethyl-2-phosphonoadipic acid and 3,5-dimethyl-3-phosphonoadipic acid.

12. A composition according to claim 8 wherein component (b) is a compound or mixture of compounds in which $R^2$, $R^3$ and $R^5$ are methyl.

13. A composition according to claim 8 wherein component (b) is a compound or mixture of compounds wherein the water-soluble inorganic salts are the sodium, potassium or ammonium salts.

14. A composition according to claim 8 wherein component (b) is a compound or mixture of compounds wherein the water-soluble organic salts are the salts of mono-, di- or triethanolamine.

* * * * *